United States Patent [19]

Guillemin et al.

[11] Patent Number: 5,480,827
[45] Date of Patent: Jan. 2, 1996

[54] USE OF POROUS POLYCRYSTALLINE ARAGONITE AS A SUPPORT MATERIAL FOR IN VITRO CULTURE OF CELLS

[75] Inventors: Geneviève Guillemin; Pascal Christel; Jean-Louis Patat, all of Paris; Alain Meunier, Coulommiers, all of France

[73] Assignee: Inoteb, Saint Gonnery, France

[21] Appl. No.: 30,134

[22] PCT Filed: Jul. 20, 1992

[86] PCT No.: PCT/FR92/00707

§ 371 Date: May 3, 1993

§ 102(e) Date: May 3, 1993

[87] PCT Pub. No.: WO93/02181

PCT Pub. Date: Feb. 4, 1993

[30] Foreign Application Priority Data

Jul. 19, 1991 [FR] France .................... 91 09205

[51] Int. Cl.$^6$ ................................... C12N 5/00
[52] U.S. Cl. ................ 435/240.23; 435/240.243
[58] Field of Search .............. 435/240.23, 174, 435/240.243

[56] References Cited

U.S. PATENT DOCUMENTS

| 3,890,107 | 6/1975 | White et al. ........................ 29/183 |
| 3,929,971 | 12/1975 | Roy ............................. 423/308 |
| 4,757,017 | 7/1988 | Cheung ......................... 435/240.23 |
| 5,153,136 | 10/1992 | Vandenbergh .................. 435/316 |
| 5,160,490 | 11/1992 | Naughton et al. ............... 435/240.23 |
| 5,230,693 | 7/1993 | Williams et al. ................. 435/174 |
| 5,262,320 | 11/1993 | Stephanopoulos et al. ....... 435/240.23 |
| 5,266,476 | 11/1993 | Sussman et al. ................ 435/240.23 |
| 5,294,551 | 3/1994 | Furcht et al. ................... 435/240.23 |
| 5,306,305 | 4/1994 | Lee ............................. 623/16 |
| 5,385,836 | 1/1995 | Kimura et al. .................. 435/177 |

FOREIGN PATENT DOCUMENTS

| 0175286 | 3/1986 | European Pat. Off. . |
| 2223325 | 10/1974 | France . |

OTHER PUBLICATIONS

Guillemin, G., et al., "Journal of Biomedical Materials Research," vol. 23(7), pp. 765–779, Jul. 1989.

Cheung, H. S., et al., "Biomaterials," vol. 10(1), pp. 63–67, Jan. 1989.

Yamaji, H., et al., "Applied Microbiology and Biotechnology," vol. 37(2), May 1992, pp. 244–251.

Guillemin, G., et al., "Journal of Biomedical Materials Research," vol. 12(5), 1987, pp. 557–567.

Doillon, C. J., "Journal of Biomaterials Applications," vol. 2, Apr. 1988, pp. 562–578.

Chemical Abstracts, vol. 111, No. 6, Aug. 1989, Abstract No. 45236h.

Chemical Abstracts, vol. 107, No. 7, Aug. 1987, Abstract No. 56902r.

*Primary Examiner*—Marian C. Knode
*Assistant Examiner*—Kristin Larson
*Attorney, Agent, or Firm*—Oliff & Berridge

[57] ABSTRACT

A three-dimensional solid support for the in vitro cultivation of cells consists essentially of porous polycrystalline aragonite in the form of a cylinder, sphere or plate. The support may be used to successively grow layers of different cells on the support, and is particularly useful for cultivating endothelial cells, fibroblasts and bone marrow cells.

8 Claims, No Drawings

USE OF POROUS POLYCRYSTALLINE ARAGONITE AS A SUPPORT MATERIAL FOR IN VITRO CULTURE OF CELLS

This application is a 371 of PCT/FR92/00707 filed in Jul. 20, 1992.

BACKGROUND

The present invention relates to the use of porous calcium carbonate, especially porous coral skeleton, as a support material for in vitro cultivation of eukaryotic or prokaryotic cells.

It is known that most eukaryotic cells can be cultivated in vitro only on a solid support. Such cultivation is generally carried out in containers or flasks in which cell multiplication stops when a monocellular layer completely covers the portion of the wall in contact with the liquid nutrient medium.

Such cultivation methods have the drawback of necessitating the handling of a large number of containers.

Moreover, eukaryotic cells do not grow on some materials, and it is not possible to predict whether a given material will be suited to the in vitro cultivation of these cells.

There is, at the present time, a considerable need for in vitro cultivation of eukaryotic cells in various fields.

For example, the in vitro cultivation of plant cells is capable of enabling natural substances to be produced and isolated without experiencing the limitations and hazards of cultivation on open ground.

Plant cells are markedly more sensitive than bacteria to the shearing effects caused by the systems usually employed in fermenters. It is hence advantageous to cultivate these cells on a solid support. Under the action of hormones, the concentration of which is defined in each case, any fragment of a plant may be cultivated in the isolated state and under sterile conditions. Undifferentiated cells (calluses) are capable of synthesizing metabolites which are normally to be found only in certain specific organs of the plant.

At the present time, medicinal active principles are the foremost substances produced, as well as various essential oils, flavorings, colorings and pesticides whose molecular complexity makes chemical synthesis too difficult and/or too expensive.

As applications of plant cell cultures, there may be mentioned:

production of anthraquinones by GALLIUM APARINE;

production of an anticancer drug, tripdiolide, by TRYTERIZHIUM WILFORDII;

production of an antispasmodic (atropine) by ATROPE BELLADONA;

production of alkaloids by PAPAVER SOMNIFERUM.

Furthermore, plant cells maintained in vitro often have strong capacities for bioconversion. For example, a salicylic acid derivative possesses faster analgesic activity than that of aspirin, as well as better gastric tolerability.

Similarly, it is desirable to be able to cultivate many animal cells in vitro, for example for medical purposes. Bone marrow cells which are precursors of the cells of the immune system are known to be very difficult to cultivate in vitro, although such cultivation is of great value in the field of allografts or autografts.

The value of a good cell multiplication in vitro extends to cells modified by genetic recombination. Up to now, such cells can, in practice, be cultivated only if they are immortalized by hybridization with cancer cells or by transformation using a virus.

Another value of the cultivation of cells in vitro would be, in a patient suffering from an existing or foreseeable loss of bone substance, the withdrawal of bone cells from this patient, the cultivation of these cells in vitro on a suitable support, and subsequently the introduction of said support comprising the cells thus cultivated in order to make good the loss of substance. It is known, in effect, that coral can constitute a biodegradable bone prosthesis, the reoccupation of which by bone as degradation takes place will be promoted by cultivated cells reintroduced in this way.

It is also advantageous to improve the methods of cultivation of cell lines such as CHO and VERO lines, or hybridomas, for the purpose of production of proteins, vaccines, hormones, antibodies, and the like.

The same applies to the cultivation of insect cells for the purpose of production of recombinant proteins or of viruses (for example baculoviruses).

Another field of interest is the cultivation of filamentous fungi, in particular ascomycetes, especially yeasts (for example Aspergillus, Penicillium, and the like). There may be mentioned, more especially, the cultivation of A. FLAVIUS for the production of aflatoxins or the cultivation of A. NIGER for the production of various organic acids.

SUMMARY OF THE INVENTION

It has now been discovered that porous calcium carbonate, especially in the form of aragonite, and in particular the skeleton of porous coral, constitutes an especially advantageous support material for the in vitro cultivation of cells, and especially of the various types of cells mentioned above.

DETAILED DESCRIPTION OF PREFERRED EMBODIMENTS

In the description below, reference will be made for convenience to the coral skeleton, which is known to consist of crystals of calcium carbonate (aragonite), or more simply to coral, but it should be pointed out that these expressions are to be interpreted here as denoting any natural or synthetic, porous calcareous material, in particular in polycrystalline form.

The subject of the present invention is hence the use of a porous material, consisting essentially of calcium carbonate, as a three-dimensional solid support for in vitro cultivation of eukaryotic cells.

For coral to be able to be used as a true three-dimensional culture support, it should be used in the form of fragments generally having dimensions larger than 0.5 mm, and especially larger than 1 mm.

This material can, for example, take the form of cylinders, spheres, plates, and the like.

Such materials may be obtained, for example, in the following manner: the pieces of crude coral are rinsed copiously with running water, dried and cut into sections, then made into the desired form having the desired dimensions, according to known methods. These sections are immersed in sodium hypochlorite solution at a concentration of 12 g/l for 48 hours, then rinsed with running water for 48 hours and dried. Finally, a sterilization by gamma radiation is performed.

One of the values of the use of the coral skeleton is that, in this skeleton, the pores communicate with one another, so that all the parts of the skeleton, even in the form of pieces of relatively large size, are usable. This communication of the pores promotes, in addition, a complete invasion of the support material by the cultivated cells, and the yield of the culture, expressed with reference to the volume of support material used, is hence optimal. This yield in volume terms is obviously high, since the coral constitutes a three-dimensional support.

It is preferable to use as support material a material having pore diameters of between 50 and 250 μm, with a porosity, that is to say pore volume relative to the total volume of the material, generally of between 20 and 80%.

This is the case, in particular, with coral of the genera Porites, Acropora, Goniopora, Lobophyllia, Symphyllia and Millipora.

Naturally, the cultivation media and conditions used according to the invention are those suited to the particular cell which is being cultivated. These culture media and conditions are well known or can be determined by simple routine experiments.

The invention relates to the use of coral skeleton as a support material in the in vitro cultivation of all eukaryotic cells, in particular plant or animal cells, including human cells.

These can be, for example, fibroblasts, endothelial cells, bone marrow cells including totipotent stem cells and osteoblasts; or alternatively transformed cells such as hybridomas, and the like.

The subject of the invention is also a method for cultivating eukaryotic cells in vitro, wherein a culture medium comprising a three-dimensional solid support made of porous calcium carbonate immersed in a suitable liquid nutrient medium is inoculated with said cells.

The support material, the culture medium and/or said eukaryotic cells are, in particular, as defined above.

Cultivation is performed at a pH suited to the multiplication of the cell being cultivated. This pH is preferably above 7 in order to avoid an appreciable dissolution of the support material. If necessary, the pH is adjusted during cultivation using a suitable pH-modifying agent.

For the cultivation of plant cells, a nutrient liquid medium containing, in particular, mineral ingredients, a nitrogen source and various additives such as, for example, HELLER's micro-ingredients is used.

Preferably, for the cultivation of plant cells, carbon and nitrogen sources, mineral and vitamin ingredients and hormones specific for preventing the shearing effects caused by the systems usually employed in fermenters are used. For the cultivation of filamentous fungi (ascomycetes), the nutrient medium contains carbon and nitrogen sources and mineral and vitamin ingredients.

Generally, the proportion by volume of the solid support relative to the total volume (liquid+solid) is greater than 5%, and especially greater than 10%; it is most often less than or equal to 50%.

To collect the cells after cultivation, if desired, it is possible to perform, for example, a trypsinization, in a known manner. In a particular embodiment, it is possible to carry out the method of the invention by cultivating two different cells of the same animal species successively on the same support. Such a method is advantageous, in particular, for cultivating certain cells such as bone marrow cells (stem cells or osteoblasts) which grow more readily on a stratum of cells (such as endothelial cells or fibroblasts) than directly on the solid support.

The subject of the invention is also the cell culture product consisting of a three-dimensional, porous calcium carbonate support occupied by eukaryotic cells, it being possible, in particular, for this culture product to be obtained according to the methods which have just been defined.

The culture product according to the invention can consist, in particular, of the solid support coated with a covering of endothelial cells or fibroblasts. The culture product of the invention can also be a support coated with such a covering which is itself coated with bone marrow stem cells and/or osteoblasts.

The examples which follow illustrate the invention without, however, limiting it.

EXAMPLE 1: CULTIVATION OF BONE MARROW CELLS

A cellular (fibroblast) coating of coral implants is prepared, and these fibroblast-coated implants are then impregnated with bone marrow from the patient.

1. Fibroblast Coating 1.1. Materials

Material: Porites coral (pore volume: 50%) in the form of disks, diameter: 30 mm, thickness: 1 mm.

Cultivation medium: M199 supplemented with 10% of fetal calf serum and 1% of antibiotics (penicillin/streptomycin).

Cell type: rat epidermal fibroblasts.

1.2. Methods

Production of a rat epidermal fibroblast culture by the explant method:

After being shaved, the skin is pinched using a curved forceps, the skin held between the two points of the forceps is then cut out with a scalpel and the fragment is placed in a saline solution containing antibiotics at high concentration (6%). Each piece is then cut up again into small squares with sharply defined edges, measuring approximately 2 mm$^2$.

The biopsies are rinsed three times in the cultivation medium containing a penicillin/streptomycin concentration 6-, 4- and then 2-fold greater than the normal concentration.

The biopsies of pieces measuring 2 mm$^2$ are cut up using "clean" cuts; they are placed in plastic cultivation dishes.

The biopsies are allowed to adhere to the support before addition of the culture medium, to which fetal calf serum will have been added in the proportion of at least 10%. Good adhesion is obtained by standing the cultivation dishes upright without medium for 40 to 60 minutes in the incubator before laying them flat.

The cultivation dishes should then be kept undisturbed and, after two or three days, the fibroblasts begin to proliferate around the explants. The medium must then be changed every two or three days. The biopsies are eliminated once proliferation has begun, and the first subculturing may be carried out. If the fibroblasts coexist in primary cultures with cells whose culture is more demanding for nutrients from the culture medium (such as myoblasts or endothelial cells), the fibroblasts are selected by impoverishment of nutrients from the cultivation medium (which fibroblasts but not the other cell types withstand). When the fibroblasts have reached confluence, that is to say contact inhibition prevents them from proliferating further, the next step, after subculturing, is three-dimensional cultivation. In this type of cultivation, the cells proliferate in all three dimensions on a three-dimensional support.

To carry out this cultivation, these cell suspensions are placed on disks of Porites coral 1 mm in diameter and 1 mm in thickness, this being done in 6-well dishes or in Petri dishes 35 mm in diameter. Quantifications of cell growth are carried out at regular intervals so as to evaluate the increase in the number of cells contained in the coral disks.

When the coral is covered with fibroblasts, the second stage is carried out: impregnation with cells contained in fresh bone marrow, either whole or after removal of non-nucleated cells (red cells and adipocytes).

2. Cultivation of Bone Marrow Cells

The bone marrow is recovered by sampling from rats into flasks containing calciparin (3 ml/500 ml). The cells are well dispersed and then placed on Ficoll in the proportion of 12 ml of Ficoll to 20 ml of marrow suspension, at 18° C. The suspension containing the cells and Ficoll is centrifuged at 1600 rpm for 20 min in a stable centrifuge not containing a brake. The stem cells can be isolated in this way.

The cultivation medium containing coral covered with fibroblasts is then inoculated with $10^7$ stem cells per ml of liquid nutrient medium.

A substantial three-dimensional growth of the bone marrow cells is observed.

Similar results are obtained by first cultivating fibroblasts of human dermis, and then human bone marrow cells.

EXAMPLE 2: CULTIVATION OF HUMAN LUNG EMBRYONIC FIBROBLAST

The support material consists of spheres or cylinders of skeleton of coral of the genus Porites. The spheres are 3 to 4 mm in diameter, the cylinders have dimensions of 3 mm in diameter and 4 mm in length.

Either coral skeleton having a 20% porosity or skeleton having a 50% porosity have been used. The cell cultivated is the MRC5 line, which is a human lung embryonic fibroblast line.

Cultivation is carried out in multiwell cultivation plates. Inoculation is performed in the proportion of 1 ml of medium containing 50,000 cells.

The cultivation medium is the Williams medium supplemented with 5% of newborn calf serum. The supports are then covered with the cultivation medium. The plates are placed in a chamber thermostated at 37° C. under a humid atmosphere (air containing 5% of $CO_2$). After 24 hours of incubation, the supports are taken up under sterile conditions and incubated in other plates containing fresh medium at 37° C., and cultivation is resumed in the supplemented Williams medium under conditions as mentioned above. The medium is then changed every two days, the total culture period being 7 days.

After 7 days of cultivation, the cellular biomass is evaluated by assaying the proteins according to the Lowry method, as well as by staining of the DNA with methylene blue.

Good cell growth is observed with the supports both in the form of spheres and in the form of cylinders.

The growth is more intense on the materials having a 20% porosity than on the materials having a 50% porosity.

EXAMPLE 3: CULTIVATION OF A HYBRIDOMA THAT PRODUCES A MONOCLONAL ANTIBODY

The hybridoma secretes an anti-folate monoclonal antibody.

It is cultivated in RPMI medium supplemented with 5% of newborn calf serum.

The other cultivation conditions are the same as those described in Example 2.

Cell growth is demonstrated using the ELISA technique to determine the quantity of monoclonal antibodies produced.

We claim:

1. A method for culturing mammalian cells in vitro comprising:

a) immersing a three-dimensional solid support in a liquid cell culture media;

b) inoculating mammalian cells in said medium; and c) culturing said cells for a time and under conditions to allow growth of said cells on said three-dimensional solid support thereby obtaining a product;

wherein said three-dimensional solid support consists of porous polycrystalline aragonite.

2. The method of claim 1 wherein said mammalian cells are selected from the group consisting of fibroblasts, endothelial cells, bone marrow cells, and osteoblasts.

3. The method of claim 2, wherein said bone marrow cells are totipotent stem cells.

4. The method of claim 1, wherein said mammalian cells are transformed cells.

5. The method of claim 1, wherein said mammalian cells are hybridomas.

6. The method of claim 1, wherein said culturing comprises culturing first cells selected from the group consisting of endothelial cells and fibroblasts on said three-dimensional solid support to form a stratum of said first cells on said support, and subsequently culturing second cells consisting of bone marrow cells on said stratum of said first cells on said support.

7. The method of claim 6, wherein said bone marrow cells are totipotent stem cells or osteoblasts.

8. The product obtained by the method of claim 1.

* * * * *